(12) United States Patent
Renati et al.

(10) Patent No.: US 8,409,238 B2
(45) Date of Patent: Apr. 2, 2013

(54) MINI CAMS ON SUPPORT LOOP FOR VESSEL STABILIZATION

(75) Inventors: Richard J. Renati, Los Gatos, CA (US); Kevin Brounstein, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1949 days.

(21) Appl. No.: 11/419,071

(22) Filed: May 18, 2006

(65) Prior Publication Data
US 2007/0270900 A1 Nov. 22, 2007

(51) Int. Cl.
*A61M 29/00* (2006.01)

(52) U.S. Cl. ............... 606/200; 606/113; 606/127

(58) Field of Classification Search .......... 606/113, 606/127, 200
See application file for complete search history.

(56) References Cited

U.S. PATENT DOCUMENTS

| | | | |
|---|---|---|---|
| 4,793,348 A | 12/1988 | Palmaz | |
| 5,814,064 A | 9/1998 | Daniel et al. | |
| 5,827,324 A | 10/1998 | Cassell et al. | |
| 5,947,995 A | 9/1999 | Samuels | |
| 6,001,118 A | 12/1999 | Daniel et al. | |
| 6,007,557 A * | 12/1999 | Ambrisco et al. | 606/200 |
| 6,129,739 A | 10/2000 | Khosravi | |
| 6,152,946 A | 11/2000 | Broome et al. | |
| 6,171,327 B1 | 1/2001 | Daniel et al. | |
| 6,179,861 B1 | 1/2001 | Khosravi et al. | |
| 6,277,138 B1 | 8/2001 | Levinson et al. | |
| 6,336,934 B1 | 1/2002 | Gilson et al. | |
| 6,371,971 B1 | 4/2002 | Tsugita et al. | |
| 6,468,298 B1 * | 10/2002 | Pelton | 623/1.11 |
| 6,494,895 B2 * | 12/2002 | Addis | 606/200 |
| 6,527,746 B1 | 3/2003 | Oslund et al. | |
| 6,530,939 B1 | 3/2003 | Hopkins et al. | |
| 6,540,722 B1 | 4/2003 | Boyle et al. | |
| 6,544,279 B1 | 4/2003 | Hopkins et al. | |
| 6,575,996 B1 | 6/2003 | Denison et al. | |
| 6,589,263 B1 | 7/2003 | Hopkins et al. | |
| 6,635,070 B2 | 10/2003 | Leeflang et al. | |
| 6,645,224 B2 | 11/2003 | Gilson et al. | |
| 6,652,554 B1 | 11/2003 | Wholey et al. | |
| 6,740,061 B1 | 5/2004 | Oslund et al. | |
| 6,878,153 B2 | 4/2005 | Linder et al. | |
| 6,878,291 B2 | 4/2005 | Lowe et al. | |
| 6,902,572 B2 | 6/2005 | Beulke et al. | |
| 6,939,361 B1 | 9/2005 | Kleshinski | |
| 6,969,396 B2 | 11/2005 | Krolik et al. | |

(Continued)

OTHER PUBLICATIONS

REI:Climbing Expert Advice web page, "How to Choose Active Rock Climbing Protection," Oct. 31, 2005, 4 pgs.

(Continued)

*Primary Examiner* — Gary Jackson
*Assistant Examiner* — Diane Yabut
(74) *Attorney, Agent, or Firm* — Seager, Tufte & Wickhem LLC (57) ABSTRACT

Embolic protection filtering devices and methods for making and using the same. An example filtering device includes a filter wire, a filter including a filter loop coupled to the filter wire, and a filter membrane coupled to the filter loop. A plurality of cam members may be coupled to the filter loop. Alternatively, the filter loop may include a plurality of strut members coupled thereto. The cam members and/or the strut members may help to stabilize the longitudinal position of the filtering device within a body lumen.

16 Claims, 5 Drawing Sheets

U.S. PATENT DOCUMENTS

| | | |
|---|---|---|
| 7,014,647 B2 | 3/2006 | Brady et al. |
| 7,060,082 B2 | 6/2006 | Goll et al. |
| 2001/0044632 A1 | 11/2001 | Daniel et al. |
| 2003/0060843 A1 | 3/2003 | Boucher |
| 2003/0187474 A1* | 10/2003 | Keegan et al. ............ 606/200 |
| 2004/0093012 A1 | 5/2004 | Cully et al. |
| 2004/0127933 A1 | 7/2004 | Demond et al. |
| 2004/0158275 A1 | 8/2004 | Crank et al. |
| 2004/0167566 A1 | 8/2004 | Beulke et al. |
| 2004/0254601 A1 | 12/2004 | Eskuri |
| 2005/0096692 A1 | 5/2005 | Linder et al. |
| 2006/0030876 A1 | 2/2006 | Peacock et al. |
| 2006/0079930 A1 | 4/2006 | McGuckin, Jr. et al. |

OTHER PUBLICATIONS

Wikipedia, the free encyclopedia, "Spring loaded camming device,", Oct. 31, 2005, 2 pgs., http://en.wikipedia.org/wiki/Spring_loaded_camming_device.

* cited by examiner

Figure 5 ic protection filtering devices. More particularly, the present invention pertains to embolic protection filtering device with position-stabilizing features and characteristics.

MINI CAMS ON SUPPORT LOOP FOR VESSEL STABILIZATION

FIELD OF THE INVENTION

The present invention pertains to embolic protection filtering devices. More particularly, the present invention pertains to embolic protection filtering device with position-stabilizing features and characteristics.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences because the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature. During angioplasty procedures, stenotic debris may also break loose due to manipulation of the blood vessel. Because of this debris, a number of devices, termed embolic protection devices, have been developed to filter out this debris.

A wide variety of filtering devices have been developed for medical use, for example, intravascular use. Of the known filtering devices, each has certain advantages and disadvantages. There is an ongoing need to provide alternative filtering devices as well as alternative methods for manufacturing filtering devices.

BRIEF SUMMARY

This disclosure pertains to design, material, and manufacturing method alternatives for filtering devices. An example filtering device includes a filter wire, a filter including a filter loop coupled to the filter wire, and a filter membrane coupled to the filter loop. A plurality of cam members may be coupled to the filter loop. Alternatively, the filter loop may include a plurality of strut members coupled thereto. The cam members and/or the strut members may help to stabilize the longitudinal position of the filtering device within a body lumen.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

DETAILED DESCRIPTION

The following description should be read with reference to the drawings wherein like reference numerals indicate like elements throughout the several views. The detailed description and drawings illustrate example embodiments of the claimed invention.

When a clinician performs an intravascular intervention such as angioplasty, atherectomy, and the like, embolic debris may dislodge from the blood vessel that can travel in the bloodstream to a position where it may impair blood flow, possibly leading to tissue damage. A number of other situations and/or interventions may also result in the mobilization of embolic debris. Accordingly, embolic protection filtering devices have been developed that can be disposed in the blood vessel downstream of the treatment site and expanded to capture debris.

Figure 1:
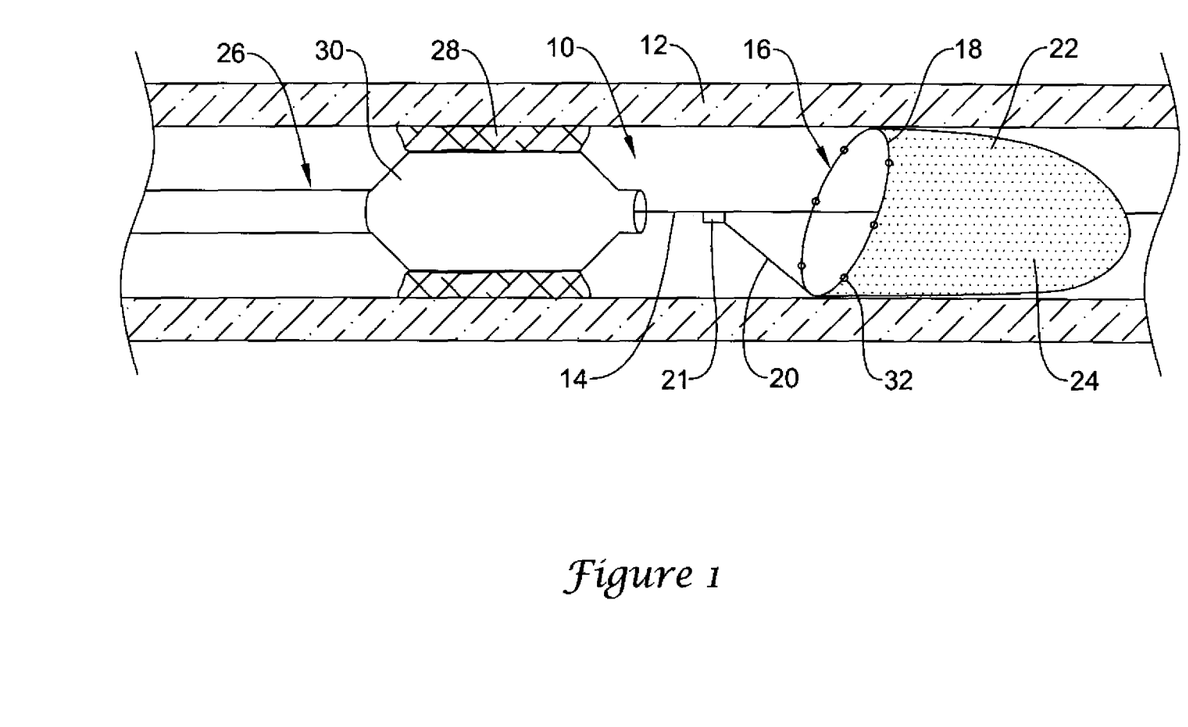
FIG. 1 is partial cross-sectional side view of an example filtering device disposed in a blood vessel.

FIG. 1 is a partial cross-sectional view of an example embolic protection filtering device 10 disposed within a blood vessel 12. Filtering device 10 can be delivered to a suitable target region, for example within blood vessel 12, using an appropriate delivery device (not shown) and removed after use with a suitable retrieval device (not shown). Device 10 may include an elongate shaft or filter wire 14 having an embolic protection filter 16 coupled thereto. Filter 16 includes a filter loop 18 and a filter membrane or fabric 22 coupled to filter loop 18. Filter membrane 22 can be drilled (for example, formed by known laser techniques) or otherwise manufactured to include a plurality of openings 24. These holes or openings 24 can be sized to allow blood flow therethrough but restrict flow of debris or emboli floating in the body lumen or cavity.

In general, filter 16 may be adapted to operate between a first generally collapsed configuration and a second generally expanded configuration for collecting debris in a body lumen. To this end, in at least some embodiments, loop 18 may be comprised of a "self-expanding" shape-memory material such as nickel-titanium alloy, which is capable of biasing filter 16 toward being in the second expanded configuration. Additionally, filter loop 18 may include a radiopaque material or include, for example, a radiopaque wire disposed about a portion thereof. Some further details regarding these and other suitable materials are provided below.

One or more struts 20 may extend between filter loop 18 and filter wire 14. Strut 20 may be coupled to filter wire 14 by a coupling 21. Coupling 21 may be one or more windings of strut 20 about filter wire 14 or may be a fitting disposed over an end of strut 20 to attach it to filter wire 14. The exact arrangement of struts 20 can vary considerably. One of ordinary skill in the art would be familiar with the various arrangements of struts 20 that are appropriate for a given intervention.

With filter 16 properly positioned in blood vessel 12, another medical device may be advanced over filter wire 14 in order to treat and/or diagnose a lesion 28. For example, a catheter 26 (such as the balloon catheter depicted in FIG. 1) may be advanced over filter wire 14 in order to expand lesion 28. Of course numerous other devices could just as easily be passed over filter wire 14 including any device designed to pass through an opening or body lumen. For example, the device may comprise any type of catheter (e.g., therapeutic, diagnostic, or guide catheter), a stent delivery catheter, an endoscopic device, a laparoscopic device, variations and refinements thereof, and the like, or any other suitable device. Alternatively, another device may be advanced over or through its own guiding structure to a suitable location adjacent filter 16 in a manner that allows device 10 to perform its intended filtering function.

Filtering device 10 is generally designed to filter embolic debris that might be generated during the course of this medical intervention. For example, device 10 can be used to capture embolic debris that might be generated during the use of catheter 26 such as when a balloon 30 (coupled to catheter 26) is inflated. It should be noted, however, that device 10 may find utility in concert with essentially any procedure that has the potential to loosen and release embolic debris in to the blood stream or with the devices associated with such procedures.

Maintaining the position of a filtering device within a blood vessel during an intervention may be desirable. For example, if the filter migrates within the vessel during an intervention, the filter could come into contact with another device (e.g., a catheter disposed on filter wire 14) and potentially interfere with the goals of the intervention. In addition, advancing other devices over the filter wire may cause small shifts in the position of the filtering device itself that takes the filtering device out of its optimal position. In at least some embodiments, the present invention addresses this potential complication by providing vessel stabilization structures that are incorporated into the design of filtering device 10 and that improve the ability of filtering device 10 to hold and/or maintain its position during an intervention.

Figure 2:
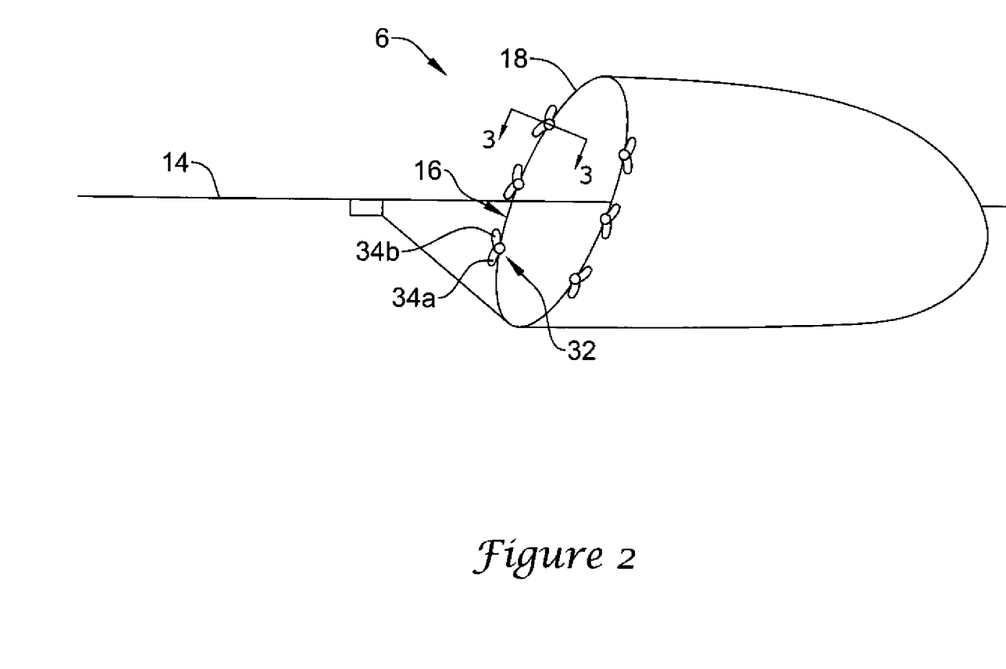
FIG. 2 is a side view of the example filtering device shown in FIG. 1.
Figure 3:
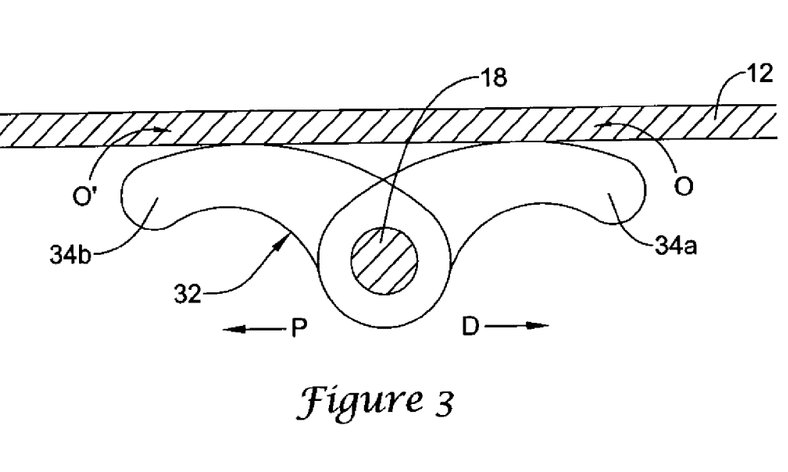
FIG. 3 is a cross-sectional view taken through line 3-3 in FIG. 2.

One of the position-stabilizing features contemplated for filtering device 10 includes one or more cam members 32 that are disposed on filter loop 18. Cam members 32, which can be more clearly seen in FIGS. 2-4, include opposing cams 34a/34b. Each of cams 34a/b is configured to project radially outward in response to force applied to filter wire 14. For example, when deployed in blood vessel 12, cam 134b may project radially outward (O') when force is applied to filter wire 14 in the proximal direction (P) whereas cam 34a may project radially outward (O) when force is applied to filter wire 14 in the distal direction (D) as depicted in FIG. 3. Because cams 34a/b oppositely project outward in response to opposite forces, cam member 32 desirably secures the position of filtering device 10 in a body lumen regardless of whether distal or proximal force is applied to filter wire 14.

Figure 4:
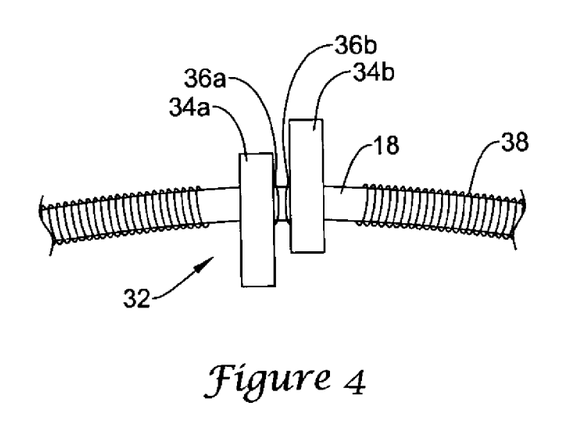
FIG. 4 is an alternative view of a portion of the example filtering device shown in FIG. 2.

Turning now to FIG. 4, here it can be seen that in some embodiments, a spring 36a/36b may be coupled to each cam 34a/34b. Springs 36a/b are generally biased to exert a force on cams 34a/34b that tends to cause cams 34a/34b to project radially inward. The bias of springs 36a/b is overcome by the application of force to filter wire 14 in either the proximal or the distal direction. For example, force applied to filter wire 14 in the distal direction overcomes the bias of spring 36a, thereby causing cam 34a to project radially outward. It should be noted that spring 36b is designed to be substantially unaffected by force applied to filter wire 14 in the distal direction. Thus, when force is applied in the distal direction to filter wire 14, spring 36b exerts force on cam 34b so that cam 34b tends to project radially inward. Conversely, force applied to filter wire 14 in the proximal direction overcomes the bias of spring 36b, thereby causing cam 34b to project radially outward. Under this condition, spring 36a is substantially unaffected and continues to exert force on cam 34a so that cam 34a tends to project radially inward.

With the above discussion in mind, it is useful to consider that in some ways, cam member 32 functions in a manner analogous to how a spring-loaded camming device, commonly used by rock climbers, functions, albeit on a smaller scale. Although not a perfect analogy, cams 34a/34b can be thought of as being roughly similar to the cams of a spring-loaded camming device and filter wire 14 can be thought of as being similar to the "trigger" of a spring-loaded camming device that causes the cams on the spring-loaded camming device to project outward when actuated.

It can also be seen in FIG. 4 that some embodiments of filtering device 10 may include a micro-coil 38 that is disposed about filter loop 18 as alluded to above. In at least some embodiments, coil 38 includes a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, molybdenum, palladium, tantalum, tungsten or tungsten alloy, plastic material loaded with a radiopaque filler, and the like. The purpose of showing coil 38 in FIG. 4 is to illustrate how coil 38 would be broken at cam members 32.

The number and arrangement of cam members 32 can vary considerably. For example, some embodiments of device 10 include one, two, three, four, five, six, seven, eight, or more cam members 32. These cam members 32 may be disposed in a regular, irregular, or any other suitable pattern about filter loop 18.

Figure 5:
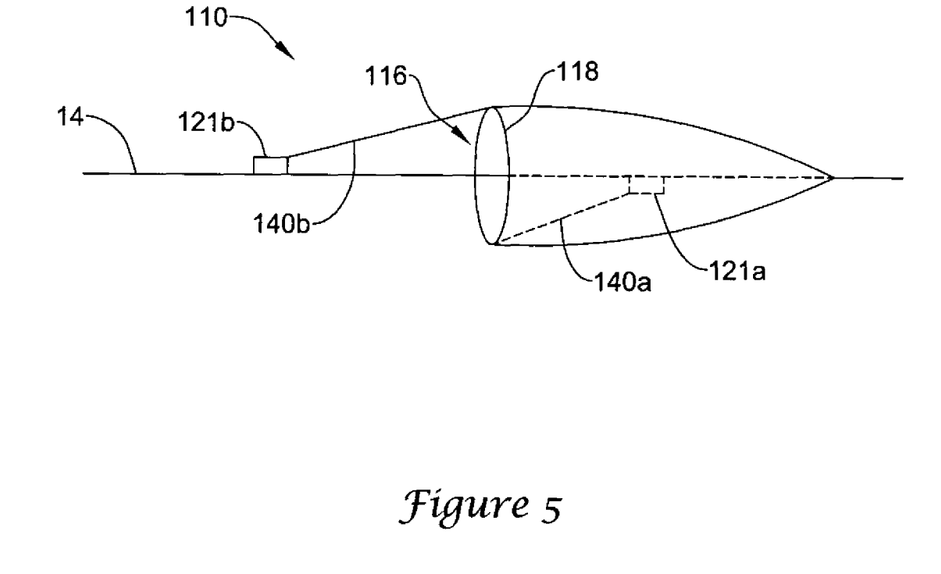
FIG. 5 is a side view of another example filtering device.

Another example filtering device 110 is illustrated in FIG. 5. Device 110 is similar in form and function to device 10 except that filtering device 110 includes a first strut member 140a coupled to filter 116 (e.g., at filter loop 118) and extending distally from filter loop 118 to filter wire 14 where it is attached by coupling 121a. Device 110 may further include a second strut member 140b coupled to filter loop 118 and extending proximally therefrom to filter wire 14 where it is attached by coupling 121b.

Figure 6:
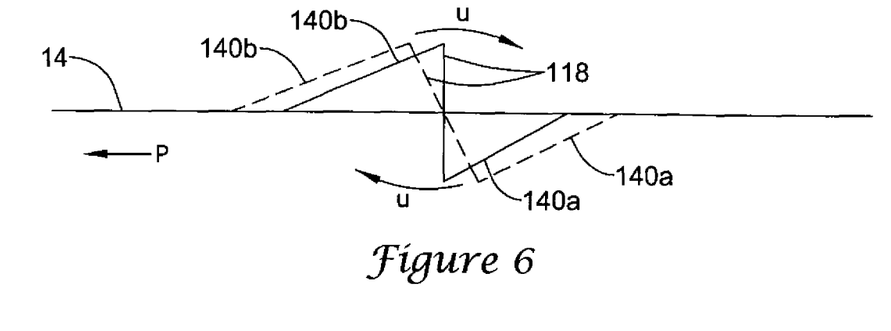
FIG. 6 is a side view of the filtering device depicted in FIG. 5 depicting what happens to the filter loop when force is applied to the shaft in the proximal direction.
Figure 7:
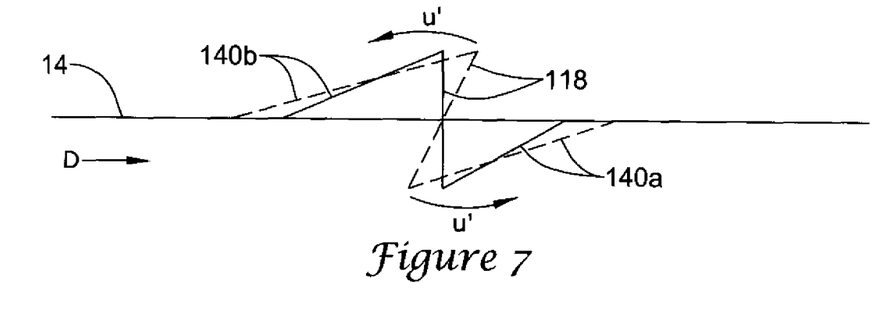
FIG. 7 is a side view of the filtering device depicted in FIG. 5 depicting what happens to the filter loop when force is applied to the shaft in the distal direction.

The way that strut members 140a/b function to longitudinally stabilize the position of filtering device 110 is shown in FIGS. 6-7. In general, strut members 140a/b are generally configured to hold filter loop 118 in an upright position. This is because each of strut members 140a/b is positioned and configured to exert a force on either the "top" of loop 118 (i.e., the top of loop 118 as depicted in FIGS. 5-7) or the "bottom" of loop 118 (i.e., the bottom of loop 118 as depicted in FIGS. 5-7). In FIG. 6, force applied to shaft 14 in the proximal direction (P) that would otherwise tend to cause filter loop 118 to lean, for example, proximally as depicted in phantom, is counteracted by upright force (U) exerted by strut members 140a/b on loop 118. Conversely, force applied in the distal direction (D) that would otherwise tend to cause filter loop 118 to lean, for example, distally as depicted in phantom, is counteracted by upright force (U') exerted by strut members 140a/b on loop 118 as depicted in FIG. 7.

The overall design of filtering devices 10/110 disclosed herein includes the use of a number of different materials appropriate for the various components thereof. These materials may include metals, metal alloys, polymers, metal-polymer composite, and the like, or any other suitable material. Some examples of suitable metals and metal alloys include stainless steel, such as 304V, 304L, and 316LV stainless steel; mild steel; nickel-titanium alloy such as linear-elastic or super-elastic nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; other Co—Cr alloys; platinum enriched stainless steel; or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly (alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An embolic protection filter, comprising:
   an elongate shaft having a proximal end region and a distal end region;
   a filter coupled to the distal end region of the shaft, the filter including a filter loop disposed about the shaft and a strut region extending between the filter loop and the shaft;
   a filter membrane coupled to the filter loop, the filter membrane having a plurality of openings defined therein; and
   a first cam member coupled to the filter loop, the first cam member being configured to move radially outward relative to the filter loop when the shaft is moved in a first direction; and
   a second cam member coupled to the first cam member, the second cam member being configured to move radially outward relative to the filter loop when the shaft is moved in a second direction that is opposite the first direction.

2. The filtering device of claim 1, further comprising one or more additional cam members coupled to the filter loop.

3. The filtering device of claim 1, further comprising one or more additional pairs of cam members coupled to the filter loop.

4. The filtering device of claim 1, further comprising a spring coupled to the first cam member, the spring being biased to exert a radially inward force on the first cam member.

5. The filtering device of claim 4, wherein movement of the shaft in the first direction overcomes the bias of the spring and exerts a radially outward force on the first cam member.

6. The filtering device of claim 1, further comprising a spring coupled to the second cam member, the spring being biased to exert a radially inward force on the second cam member.

7. The filtering device of claim 6, wherein movement of the shaft in the second direction overcomes the bias of the spring and exerts a radially outward force on the second cam member.

8. The filtering device of claim 1, further comprising a spring coupled to the second cam member, the spring being biased to exert a radially inward force on the second cam member.

9. The filtering device of claim 8, wherein movement of the elongate filter wire in the second direction overcomes the bias of the spring and exerts a radially outward force on the second cam member.

10. An embolic protection filter, comprising:
    an elongate filter wire having a proximal end region and a distal end region;
    a filter coupled to the distal end region of the filter wire, the filter including a filter loop disposed about the filter wire and a strut region extending between the filter loop and the filter wire;
    a filter membrane coupled to the filter loop, the filter membrane having a plurality of openings defined therein;
    a cam member coupled to the filter loop, the cam member including a first cam and a second cam, the first cam member being configured to project radially outward and distally relative to the filter loop when the filter wire is moved in a first direction and the second cam member being configured to project radially outward and proximally relative to the filter loop when the filter wire is moved in a second direction that is opposite the first direction.

11. The filtering device of claim 10, further comprising one or more additional cam members coupled to the filter loop.

12. The filtering device of claim 10, further comprising one or more additional pairs of cam members coupled to the filter loop.

13. The filtering device of claim 10, further comprising a spring coupled to the first cam member, the spring being biased to exert a radially inward force on the first cam member.

14. The filtering device of claim 13, wherein movement of the elongate filter wire in the first direction overcomes the bias of the spring and exerts a radially outward force on the first cam member.

15. The filtering device of claim 10, wherein the first direction is a proximal direction.

16. The filtering device of claim 15, wherein the second direction is a distal direction.

* * * * *

UNITED STATES PATENT AND TRADEMARK OFFICE
CERTIFICATE OF CORRECTION

| | | |
|---|---|---|
| PATENT NO. | : 8,409,238 B2 | Page 1 of 1 |
| APPLICATION NO. | : 11/419071 | |
| DATED | : April 2, 2013 | |
| INVENTOR(S) | : Richard J. Renati and Kevin Brounstein | |

It is certified that error appears in the above-identified patent and that said Letters Patent is hereby corrected as shown below:

In the Specification

Column 3
Line 14: delete "laparoscopic" and insert -- laproscopic --.

Column 3
Line 50: delete "cam 134b" and insert -- cam 34a --.

Signed and Sealed this
Sixteenth Day of July, 2013

Teresa Stanek Rea
*Acting Director of the United States Patent and Trademark Office*